US00PP26400P3

(12) United States Plant Patent
Crowther

(10) Patent No.: US PP26,400 P3
(45) Date of Patent: Feb. 2, 2016

(54) ***HYPERICUM* PLANT NAMED 'CROWTHYP'**

(50) Latin Name: *Hypericum calycinum*
Varietal Denomination: CROWTHYP

(71) Applicant: Timothy Crowther, Walberton (GB)

(72) Inventor: Timothy Crowther, Walberton (GB)

( * ) Notice: Subject to any disclaimer, the term of this patent is extended or adjusted under 35 U.S.C. 154(b) by 118 days.

(21) Appl. No.: 14/120,324

(22) Filed: May 15, 2014

(65) Prior Publication Data

US 2014/0345024 P1 Nov. 20, 2014

Related U.S. Application Data

(60) Provisional application No. 61/855,662, filed on May 20, 2013.

(51) Int. Cl.
*A01H 5/00* (2006.01)
*A01H 5/02* (2006.01)

(52) U.S. Cl.
USPC ..... Plt./442
CPC ..... *A01H 5/02* (2013.01)

(58) Field of Classification Search
USPC ..... Plt./442
See application file for complete search history.

*Primary Examiner* — Annette Para
(74) *Attorney, Agent, or Firm* — James M. Weatherly; Barbara Campbell; Cochran Freund & Young LLC

(57) ABSTRACT

A new cultivar of *Hypericum* plant named 'CROWTHYP' that is characterized by a prostrate and spreading habit, variegated green and cream-yellow, with pink coloration to its new growth, single and bright flowers lemon-yellow in color with numerous lemon-yellow stamens bearing prominent mid-brown anthers, hardy to USDA Zone 5, is disclosed.

2 Drawing Sheets

Genus and species: *Hypericum calycinum.*
Variety denomination: 'CROWTHYP'.

BACKGROUND OF THE NEW PLANT

The present invention relates to a new and distinct cultivar of *Hypericum*, which is grown as an ornamental plant for use in the garden and as a ground cover plant in the landscape. The new cultivar is known botanically as *Hypericum calycinum*, and will be referred to hereinafter by the cultivar name 'CROWTHYP'. 'CROWTHYP' was discovered in 2008 as a naturally occurring branch mutation on a plant of the species *Hypericum calycinum* (unpatented) which was growing in a cultivated garden near Belves, Department 24 Dordogne, Region Aquitaine, France. The branch mutation exhibited green and gold variegation. The resulting plant is both attractive and striking in the landscape both in and out of flower.

'CROWTHYP' exhibits a prostrate, spreading growth habit and prominently variegated foliage that is multicolored green, lemon and line, with pink coloration to its new growth. 'CROWTHYP' grows to 20 cm in height and 30 cm in width during a one year growing season. 'CROWTHYP' exhibits its distinguishing characteristics to best effect when grown in full sun or light shade, with moderate water. There are no particular pests or diseases known to the inventor which affect 'CROWTHYP'. 'CROWTHYP' is hardy to USDA Zone 5.

'CROWTHYP' was first asexually propagated in 2008 in Arundel, West Sussex, United Kingdom. The branch mutation was excised from the parent plant and established as a plant on its own roots. Subsequently, in 2009 and 2010 additional plants were propagated by softwood stem cuttings. Since that time under careful observation, the distinguishing characteristics have been determined stable, uniform, and to be reproduced true to type in subsequent generations of asexual propagation.

SUMMARY

The following traits have been repeatedly observed and represent the distinguishing characteristics of the new *Hypericum* cultivar named 'CROWTHYP'. These traits in combination distinguish 'CROWTHYP' from all other existing varieties of *Hypericum* known to the inventor. 'CROWTHYP' has not been tested under all possible conditions and phenotypic differences may be observed with variations in environmental, climatic, and cultural conditions, however, without any variance in genotype.

1. 'CROWTHYP' exhibits a prostrate and spreading habit.
2. The foliage of 'CROWTHYP' is variegated green and cream-yellow, with pink coloration to its new growth.
3. The flowers of 'CROWTHYP' are single and bright lemon-yellow in color with numerous lemon-yellow stamens bearing prominent mid-brown anthers.
4. The flowers of 'CROWTHYP' are 5 cm to 6 cm in diameter.
5. After one year of growth, plants of 'CROWTHYP' are 20 cm to 30 cm in height and 30 cm to 45 cm in width.
6. 'CROWTHYP' prefers moist well drained soil and is drought tolerant once established.
7. 'CROWTHYP' is hardy to USDA Zone 5.

COMPARISON WITH PARENTAL LINE AND KNOWN VARIETY

The two closest comparison plants are the non-variegated parent variety, species *Hypericum calycinum* (unpatented), and the variegated variety known as *Hypericum×moserianum* 'Tricolor' (unpatented). 'CROWTHYP' is distinguishable from the parent variety by its variegated leaves. In other respects, including the lemon-yellow flowers, 'CROWTHYP' is indistinguishable from its parent. 'CROWTHYP' may be distinguished from 'Tricolor' by the degree and color of variegation. Whereas 'CROWTHYP' exhibits striking bright cream-yellow variegation, the variegation of 'Tricolor' consists of slender pale cream margins.

'CROWTHYP' may also be distinguished from many varieties of *Hypericum* which have been hybridized and released for their colorful fruit (berries) borne on stems which are cut and used in floral arrangements. The variegated foliage is the primary market characteristic of 'CROWTHYP' which is not grown for its flowers or fruit.

BRIEF DESCRIPTION OF THE PHOTOGRAPHS

The accompanying color photographs labeled FIG. 1 and FIG. 2 illustrate the overall appearance of 'CROWTHYP' showing the colors as true as is reasonably possible to obtain in colored reproductions of this type. Colors in the photographs may differ from the color values cited in the detailed botanical description, which accurately describes the actual colors of 'CROWTHYP'.

Figure 1:
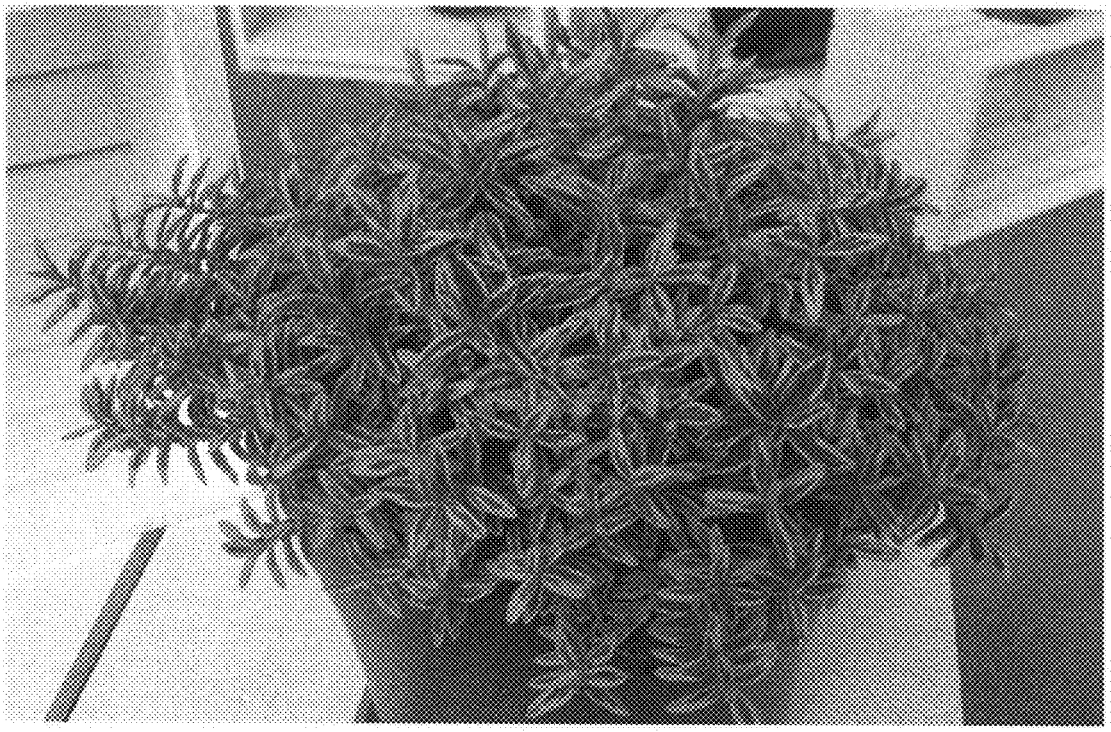
FIG.1 depicts an entire plant of 'CROWTHYP' which is 15 months old from a cutting. The plant has been grown out doors in a 2 gallon container in Oxnard, Calif.
Figure 2:
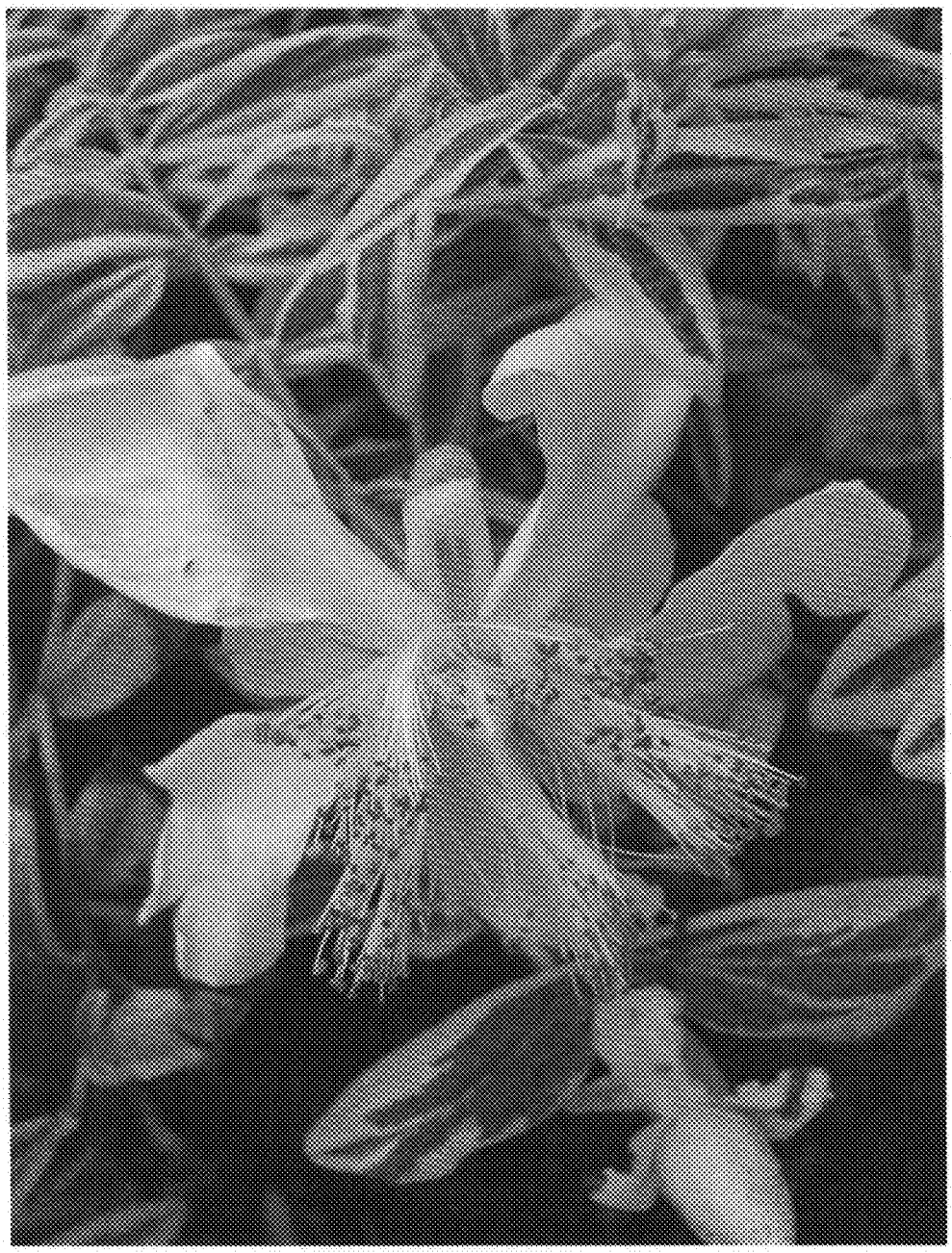
FIG. 2 depicts a close-up view of the flower of 'CROWTHYP'.

All photographs were made from one year old plants which have been grown in 1.5-liter containers in a cold glasshouse in Devon, United Kingdom. No chemicals were used to treat the plants.

All photographs were made using conventional techniques and although colors may appear different from actual colors due to light reflectance they are as accurate as possible by conventional photography.

BOTANICAL DESCRIPTION OF THE PLANT

The following is a detailed botanical description of the new *Hypericum* cultivar named 'CROWTHYP'. Observations, measurements, values and comparisons were collected in Santa Barbara, Calif. from a 1 year old plant grown in the landscape. Color determinations were made in accordance with The 2007 Royal Horticultural Society Colour Chart from London England, except where general color terms of ordinary dictionary significance are used. Growing requirements are similar to the species.

Botanical classification: *Hypericum calycinum* 'CROWTHYP'.

- *Family*.—Hypericaceae.
- *Genus.—Hypericum.*
- *Species.—calycinum.*
- *Denomination*.—'CROWTHYP'.
- *Common name.—Hypericum.*
- *Parentage*.—The new variety *Hypericum calycinum* 'CROWTHYP' was discovered as a naturally occurring variegated branch sport on a plant of the species *Hypericum calycinum*. (unpatented).

Plant description:

- *Plant habit*.—Compact clump-forming, becoming prostrate when mature.
- *Dimensions*.—After one year of growth, plants of 'CROWTHYP' are 20 cm to 30 cm in height and 30 cm to 45 cm in width.
- *Blooming period*.—Late summer and fall.
- *Cold hardiness*.—Hardy in U.S.D.A. Zone 5.
- *Pest and diseases resistance or susceptibility*.—None known to the inventor.
- *Root description*.—Fibrous.
- *Propagation*.—Softwood stem cuttings.
- *Crop time*.—12 to 15 months from a cutting, in a 1 gallon container.
- *Soil preference*.—Prefers moist well drained soil and is drought-tolerant once established.
- *Growth rate*.—Moderate.

Stem description:

- *Shape*.—Cylindrical.
- *Stem color*.—138B, except 174C where exposed to sunlight (upper surfaces).
- *Stem dimensions*.—18 cm to 20 cm in length and 2 mm in width.
- *Stem surface*.—Smooth, matte.
- *Internode length*.—1.0 cm to 1.5 cm.
- *Branching*.—Vigorous basal branching.

Foliage description:

- *Leaf shape*.—Ovate.
- *Leaf division*.—Simple.
- *Leaf base*.—Cuneate.
- *Leaf apex*.—Acute.
- *Leaf fragrance*.—None.
- *Leaf venation*.—Pinnate, fine, faint on adaxial surface, color (both surfaces) 156D.
- *Leaf margins*.—Smooth, entire.
- *Leaf arrangement*.—Opposite.
- *Leaf attachment*.—Sessile.
- *Leaf surface*.—Upper surface smooth and glabrous; lower surface rough and dull.
- *Leaf size*.—2.5 cm to 3.5 cm in length; 1.5 cm to 1.8 cm in width.
- *Leaf variegation pattern*.—Approximately one-half to two-thirds of the leaf surface exhibits cream to golden yellow margins which extend from 2 mm to 4 mm inward from leaf margin. The remaining central portion of each leaf is predominantly mid-green. Recently emerging leaves are tinged with pink coloration on their adaxial marginal surfaces.
- *Leaf colors* (*upper surface*).—Towards margins: Ranges between 12A and 12C, with pink coloration as leaf emerges. Center of leaf: 137B.
- *Leaf colors* (*lower surface*).—Towards margins: 11B. Center of leaf: 194A.

Inflorescence description:

- *Inflorescence type*.—Terminal, borne singly.
- *Inflorescence shape*.—Rotate.
- *Dimensions*.—5 cm to 6 cm in diameter and 5 mm in depth.
- *Flowering period*.—Flowers present from late summer, very short-lasting (1 to 2 days).

Flower buds:

- *Dimensions*.—Length 2.0 cm to 2.5 cm; diameter 1 cm.
- *Shape*.—Ovate.
- *Color*.—2B.
- *Surface*.—Glabrous.

Peduncles:

- *Shape*.—Cylindrical.
- *Dimensions*.—2.0 cm to 2.5 cm in length and 2 mm in diameter.
- *Color*.—138B, except 174C where exposed to sunlight.
- *Surface*.—Smooth, matte.

Pedicels:

- *Absent*.—Flowers are borne singly.

Sepals:

*Number.*—5.

*Shape*.—Ovate, base truncate, apex rounded.

*Dimensions.*—5 mm in length and 3 mm in width.

*Margin*.—Entire.

*Surface*.—Smooth, glabrous.

*Color* (*both surfaces*).—12C.

Petals:

*Number.*—5, unfused and spaced widely apart.

*Shape*.—Irregularly ovate.

*Dimensions.*—2.0 cm to 2.5 cm in length and 1 cm in width.

*Base*.—Truncate.

*Apex*.—Rounded.

*Margin*.—Entire.

*Surface*.—Smooth, glabrous.

*Color* (*both surfaces*).—2B.

Reproductive organs:

*Stamens*.—Numerous, approximately 125 to 150.

*Filaments*.—Length 2 cm; fine, diameter less than 0.5 mm; color cream-yellow 12C becoming pure white (translucent) towards anthers.

*Anthers*.—Ovoid, basifixed, 3 mm in length, 2 mm in width, color 167B.

*Pollen*.—None observed.

*Pistil*.—1, length 10 mm to 12 mm, diameter 2 mm. Color 2B.

*Stigma*.—Absent.

*Ovary*.—Superior, obconical, diameter 6 mm to 8 mm, height 6 mm to 8 mm, color 2B.

Fruit and seed: No fruit or seed production has been observed.

I claim:

1. A new and distinct cultivar of *Hypericum* plant named 'CROWTHYP' as described and illustrated herein.

* * * * *